(12) United States Patent
Govari et al.

(10) Patent No.: US 11,000,201 B2
(45) Date of Patent: May 11, 2021

(54) COILS FORMED IN FOLDED NITINOL SHEET

(71) Applicant: BIOSENSE WEBSTER (ISRAEL) LTD., Yokneam (IL)

(72) Inventors: Assaf Govari, Haifa (IL); Andres Claudio Altmann, Haifa (IL); Christopher Thomas Beeckler, Brea, CA (US); Joseph Thomas Keyes, Glendora, CA (US); Kevin Justin Herrera, West Covina, CA (US); Jiayin Liu, Covina, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 808 days.

(21) Appl. No.: 15/347,242

(22) Filed: Nov. 9, 2016

(65) Prior Publication Data

US 2018/0125382 A1    May 10, 2018

(51) Int. Cl.
*A61B 5/03*      (2006.01)
*A61B 18/14*     (2006.01)
(Continued)

(52) U.S. Cl.
CPC .............. *A61B 5/03* (2013.01); *A61B 5/283* (2021.01); *A61B 5/6852* (2013.01); *A61B 5/6885* (2013.01); *A61B 18/1492* (2013.01); *A61B 34/20* (2016.02); *A61B 2017/003* (2013.01); *A61B 2017/00862* (2013.01);
(Continued)

(58) Field of Classification Search
CPC .............. A61B 5/6852; A61B 18/1492; A61B 2017/00862; A61B 2017/003; A61B 2090/065; A61B 5/03; A61B 5/6885; A61M 39/10; A61M 39/12; A61M 25/0074; A61M 25/0138; A61M 25/0069; A61M 2025/0002; A61M 25/0141; A61M 39/1011; A61M 2039/1066; A61M 25/0054; A61M 2205/0266; A61M 2025/0175; F16L 33/225; F16L 33/2071; F16L 32/005; F16L 37/0925;
(Continued)

(56) References Cited

U.S. PATENT DOCUMENTS 4,632,435 A * 12/1986 Polyak ...................... B25B 7/02
                                                              285/179
6,226,542 B1   5/2001 Reisfeld
(Continued)

FOREIGN PATENT DOCUMENTS

EP     2 347 726 A2      7/2011
WO  WO 2007/050960 A2   5/2007
WO  WO 2015/123583 A1   8/2015

OTHER PUBLICATIONS

Pending U.S. Appl. No. 14/937,998, filed Nov. 11, 2015.
(Continued)

*Primary Examiner* — Devin B Henson

(57) ABSTRACT

A contact force sensor is constructed using a spring in which a resilient member is interposed between two contacting elements. Extensions connected to the resilient member are in contact with the elements. A force applied to at least one of the elements causes a deformation of the spring that correlates with a displacement of the elements relative to one another.

1 Claim, 8 Drawing Sheets

(51) Int. Cl.
*A61B 5/283* (2021.01)
*A61B 5/00* (2006.01)
*A61B 34/20* (2016.01)
*A61B 17/00* (2006.01)
*A61B 18/00* (2006.01)
*A61B 90/00* (2016.01)

(52) U.S. Cl.
CPC .............. *A61B 2017/00867* (2013.01); *A61B 2018/00023* (2013.01); *A61B 2018/00196* (2013.01); *A61B 2018/00351* (2013.01); *A61B 2018/00357* (2013.01); *A61B 2018/00577* (2013.01); *A61B 2018/00815* (2013.01); *A61B 2018/00821* (2013.01); *A61B 2018/00839* (2013.01); *A61B 2018/00875* (2013.01); *A61B 2034/2051* (2016.02); *A61B 2034/2053* (2016.02); *A61B 2034/2072* (2016.02); *A61B 2090/065* (2016.02); *A61B 2562/0247* (2013.01)

(58) Field of Classification Search
CPC ... F16L 33/221; F16L 33/222; F16L 37/0842; F16L 37/086; F16L 37/096
USPC ..... 606/34, 41; 604/530, 533; 285/257, 243, 285/235
See application file for complete search history.

(56) References Cited

U.S. PATENT DOCUMENTS

| | | |
|---|---|---|
| 6,301,496 B1 | 10/2001 | Reisfeld |
| 6,695,808 B2 | 2/2004 | Tom |
| 6,814,733 B2 | 11/2004 | Schwartz et al. |
| 6,892,091 B1 | 5/2005 | Ben-Haim |
| 6,997,924 B2 | 2/2006 | Schwartz et al. |
| 7,156,816 B2 | 1/2007 | Schwartz et al. |
| 7,536,218 B2 | 5/2009 | Govari et al. |
| 7,756,576 B2 | 7/2010 | Levin |
| 8,515,521 B2 | 8/2013 | Erdman et al. |
| 8,926,604 B2 | 1/2015 | Govari et al. |
| 2003/0187347 A1 | 10/2003 | Nevo |
| 2007/0088326 A1* | 4/2007 | Kennedy, II .......... A61M 39/10 604/533 |
| 2009/0093806 A1* | 4/2009 | Govari .................... A61B 5/06 606/34 |
| 2009/0306650 A1* | 12/2009 | Govari .................. A61B 5/062 606/41 |

OTHER PUBLICATIONS

European Search Report dated Jan. 29, 2018 from corresponding European Patent Application No. 17200653.8.
European Search Report for corresponding EPA No. 19189057.3 dated Oct. 18, 2019.

* cited by examiner

COILS FORMED IN FOLDED NITINOL SHEET

COPYRIGHT NOTICE

A portion of the disclosure of this patent document contains material that is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND OF THE INVENTION

1. Field of the Invention

This invention relates to hollow probes and catheters. More particularly, this invention relates to a catheter having a contact force sensor.

2. Description of the Related Art

Cardiac arrhythmias, such as atrial fibrillation, occur when regions of cardiac tissue abnormally conduct electric signals to adjacent tissue, thereby disrupting the normal cardiac cycle and causing asynchronous rhythm.

Procedures for treating arrhythmia include surgically disrupting the origin of the signals causing the arrhythmia, as well as disrupting the conducting pathway for such signals. By selectively ablating cardiac tissue by application of energy via a catheter, it is sometimes possible to cease or modify the propagation of unwanted electrical signals from one portion of the heart to another. The ablation process destroys the unwanted electrical pathways by formation of non-conducting lesions.

Verification of physical electrode contact with the target tissue is important for controlling the delivery of ablation energy. Attempts in the art to verify electrode contact with the tissue have been extensive, and various techniques have been suggested. For example, U.S. Pat. No. 6,695,808 describes apparatus for treating a selected patient tissue or organ region. A probe has a contact surface that may be urged against the region, thereby creating contact pressure. A pressure transducer measures the contact pressure. This arrangement is said to meet the needs of procedures in which a medical instrument must be placed in firm but not excessive contact with an anatomical surface, by providing information to the user of the instrument that is indicative of the existence and magnitude of the contact force.

Commonly assigned application Ser. No. 14/937,998 to Bonyak et al., which is herein incorporated by reference, describes a symmetric contact force sensor in a probe. A resilient member couples the tip to the distal portion of the probe and is configured to deform in response to pressure exerted on the tip when engaging tissue. A position sensor in the distal portion of the probe senses the position of the tip relative to the distal portion of the probe. The relative position changes in response to deformation of the resilient member. The position sensor generates a signal indicative of the position of the tip responsively to a magnetic field produced by a magnetic field generator located in the position sensor.

SUMMARY OF THE INVENTION

Springs that are found in conventional contact force sensors are individually prepared, for example by cutting from nitinol tubing. Embodiments of the invention provide catheters with contact force sensors and methods for producing the catheters using spring designs cut from planar sheet metal and shape-set into final form. The designs are adapted to mass production and can be accommodated in small spaces as required for contact force sensors in medical catheters.

There is provided according to embodiments of the invention an apparatus, in which a spring has a resilient member interposed between two contacting elements. Extensions connected to the resilient member are in contact with the elements, wherein a force applied to at least one of the elements causes a deformation of the spring that correlates with a displacement of the elements relative to one another.

According to one aspect of the apparatus, the resilient member includes a central ring, wherein first segments of the ring are disposed on one side of a plane and the second segments are disposed on another side of the plane. The deformation includes approximating the first segments and the second segments to the plane.

According to another aspect of the apparatus, the resilient member includes a central ring having a sinusoidal configuration with radial oscillations toward and away from a central point of the ring.

According to one aspect of the apparatus the resilient member includes a central ring including a plurality of sectors, each of the sectors formed into two hairpin curves.

According to a further aspect of the apparatus, the deformation includes a torsion of at least one of the elements relative to another of the elements.

According to a further aspect of the apparatus, the extensions comprise a plurality of legs attached to a central ring, wherein first legs and second legs extend respectively in opposite first and second perpendicular directions to the ring.

In yet another aspect of the apparatus includes first links and second links connect the first legs and the second legs to the ring at opposite angles with respect to a plane, respectively, wherein the deformation includes a reduction in the angles.

According to still another aspect of the apparatus, the first legs and the second legs contact end surfaces of respective elements.

According to an additional aspect of the apparatus, the first legs and the second legs embrace respective elements.

There is further provided according to embodiments of the invention an apparatus, including a flexible insertion tube, having a proximal portion and a distal portion for insertion into a body cavity of a patient, and a resilient member, which couples the proximal portion of the insertion tube to the distal portion. The resilient member is formed of shape-set elastic material and has proximal and distal extensions in contact with the proximal portion and the distal portion of the insertion tube, respectively. A force applied through the distal portion produces a deformation of the resilient member that correlates with a displacement of the proximal portion relative to the distal portion.

There is further provided according to embodiments of the invention a method of manufacturing a medical probe, which is carried out by providing an elongated probe having a proximal portion and a distal portion. The distal portion has an electrode disposed thereon. The method is further carried out by forming a resilient member from sheet metal, the resilient member having an elastic portion and an attachment portion. The attachment portion is configured to engage the proximal portion and the distal portion of the probe. The method is further carried out by shape-setting the resilient member, and configuring the resilient member as a contact force sensor by coupling the resilient member to the proximal portion and to the distal portion so that a force applied through the distal portion produces a deformation of the resilient member that correlates with a displacement of the proximal portion relative to the distal portion.

According to an aspect of the method, forming a resilient member includes cutting a spring form from sheet metal.

According to still another aspect of the method, cutting is performed by laser cutting.

According to an additional aspect of the method, forming a resilient member includes stamping a spring form from sheet metal.

According to another aspect of the method, the sheet metal can be thin-film sputtered nitinol, cold-worked nitinol, beryllium-copper alloy, cobalt chromium alloy, or stainless steel alloy.

According to one aspect of the method, shape-setting is performed by heating the sheet metal in an oven.

According to an additional aspect of the method, shape-setting is performed by hot forming the sheet metal as part of a stamping process.

According to a further aspect of the method, stamping includes progressive stamping with a series of dies.

BRIEF DESCRIPTION OF THE SEVERAL VIEWS OF THE DRAWINGS

For a better understanding of the present invention, reference is made to the detailed description of the invention, by way of example, which is to be read in conjunction with the following drawings, wherein like elements are given like reference numerals, and wherein.

DETAILED DESCRIPTION OF THE INVENTION

In the following description, numerous specific details are set forth in order to provide a thorough understanding of the various principles of the present invention. It will be apparent to one skilled in the art, however, that not all these details are necessarily needed for practicing the present invention. In this instance, well-known circuits, control logic, and the details of computer program instructions for conventional algorithms and processes have not been shown in detail in order not to obscure the general concepts unnecessarily.

Documents incorporated by reference herein are to be considered an integral part of the application except that, to the extent that any terms are defined in these incorporated documents in a manner that conflicts with definitions made explicitly or implicitly in the present specification, only the definitions in the present specification should be considered. System Overview.

Figure 1:
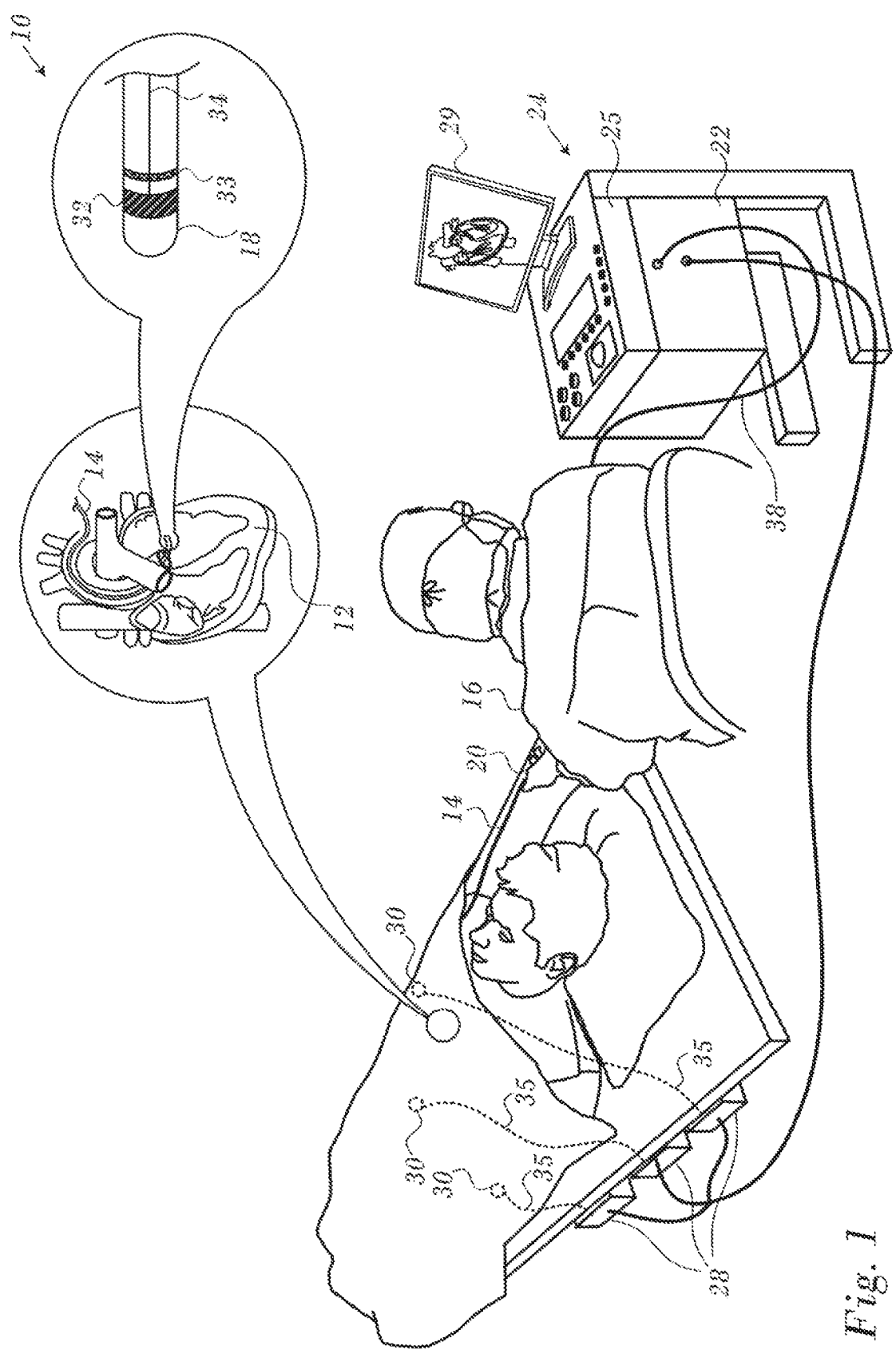
FIG. 1 is a pictorial illustration of a system for performing catheterization procedures on a heart, in accordance with a disclosed embodiment of the invention.

Turning now to the drawings, reference is initially made to FIG. 1, which is a pictorial illustration of a system 10 for evaluating electrical activity and performing ablative procedures on a heart 12 of a living subject, which is constructed and operative in accordance with a disclosed embodiment of the invention. The system comprises a catheter 14, which is percutaneously inserted by an operator 16 through the patient's vascular system into a chamber or vascular structure of the heart 12. The operator 16, who is typically a physician, brings the catheter's distal tip 18 into contact with the heart wall, for example, at an ablation target site. Electrical activation maps may be prepared, according to the methods disclosed in U.S. Pat. Nos. 6,226,542, and 6,301,496, and in commonly assigned U.S. Pat. No. 6,892,091, whose disclosures are herein incorporated by reference. One commercial product embodying elements of the system 10 is available as the CARTO® 3 System, available from Biosense Webster, Inc., 3333 Diamond Canyon Road, Diamond Bar, Calif. 91765. This system may be modified by those skilled in the art to embody the principles of the invention described herein.

Areas determined to be abnormal, for example by evaluation of the electrical activation maps, can be ablated by application of thermal energy, e.g., by passage of radiofrequency electrical current through wires in the catheter to one or more electrodes at the distal tip 18, which apply the radiofrequency energy to the myocardium. The energy is absorbed in the tissue, heating it to a point (typically about 60° C.) at which it permanently loses its electrical excitability. When successful, this procedure creates non-conducting lesions in the cardiac tissue, which disrupt the abnormal electrical pathway causing the arrhythmia. The principles of the invention can be applied to different heart chambers to diagnose and treat many different cardiac arrhythmias.

The catheter 14 typically comprises a handle 20, having suitable controls on the handle to enable the operator 16 to steer, position and orient the distal portion of the catheter as desired for the ablation. To aid the operator 16, the distal portion of the catheter 14 contains position sensors (not shown) that provide signals to a processor 22, located in a console 24. The processor 22 may fulfill several processing functions as described below. In addition the catheter 14 comprises a contact force sensor, which is described below.

Ablation energy and electrical signals can be conveyed to and from the heart 12 through one or more ablation electrodes 32 located at or near the distal tip 18 via cable 34 to the console 24. Pacing signals and other control signals may be conveyed from the console 24 through the cable 34 and the electrodes 32 to the heart 12. Sensing electrodes 33, also connected to the console 24 are disposed between the ablation electrodes 32 and have connections to the cable 34.

Wire connections 35 link the console 24 with body surface electrodes 30 and other components of a positioning sub-system for measuring location and orientation coordinates of the catheter 14. The processor 22 or another processor (not shown) may be an element of the positioning subsystem. The electrodes 32 and the body surface electrodes 30 may be used to measure tissue impedance at the ablation site as taught in U.S. Pat. No. 7,536,218, issued to Govari et al., which is herein incorporated by reference. A temperature sensor (not shown), typically a thermocouple or thermistor, may be mounted on or near each of the electrodes 32.

The console 24 typically contains one or more ablation power generators 25. The catheter 14 may be adapted to conduct ablative energy to the heart using any known ablation technique, e.g., radiofrequency energy, ultrasound energy, and laser-produced light energy. Such methods are disclosed in commonly assigned U.S. Pat. Nos. 6,814,733, 6,997,924, and 7,156,816, which are herein incorporated by reference.

In one embodiment, the positioning subsystem comprises a magnetic position tracking arrangement that determines the position and orientation of the catheter 14 by generating magnetic fields in a predefined working volume and sensing these fields at the catheter, using field generating coils 28. The positioning subsystem is described in U.S. Pat. No. 7,756,576, which is hereby incorporated by reference, and in the above-noted U.S. Pat. No. 7,536,218.

As noted above, the catheter 14 is coupled to the console 24, which enables the operator 16 to observe and regulate the functions of the catheter 14. Console 24 includes a processor, preferably a computer with appropriate signal processing circuits. The processor is coupled to drive a monitor 29. The signal processing circuits typically receive, amplify, filter and digitize signals from the catheter 14, including signals generated by sensors such as electrical, temperature and contact force sensors, and a plurality of location sensing electrodes (not shown) located distally in the catheter 14. The digitized signals are received and used by the console 24 and the positioning system to compute the position and orientation of the catheter 14, and to analyze the electrical signals from the electrodes.

In order to generate electroanatomic maps, the processor 22 typically comprises an electroanatomic map generator, an image registration program, an image or data analysis program and a graphical user interface configured to present graphical information on the monitor 29.

Typically, the system 10 includes other elements, which are not shown in the figures for the sake of simplicity. For example, the system 10 may include an electrocardiogram (ECG) monitor, coupled to receive signals from one or more body surface electrodes, in order to provide an ECG synchronization signal to the console 24. As mentioned above, the system 10 typically also includes a reference position sensor, either on an externally-applied reference patch attached to the exterior of the subject's body, or on an internally-placed catheter, which is inserted into the heart 12 maintained in a fixed position relative to the heart 12. Conventional pumps and lines for circulating liquids through the catheter 14 for cooling the ablation site are provided. The system 10 may receive image data from an external imaging modality, such as an MRI unit or the like and includes image processors that can be incorporated in or invoked by the processor 22 for generating and displaying images.

Figure 2:
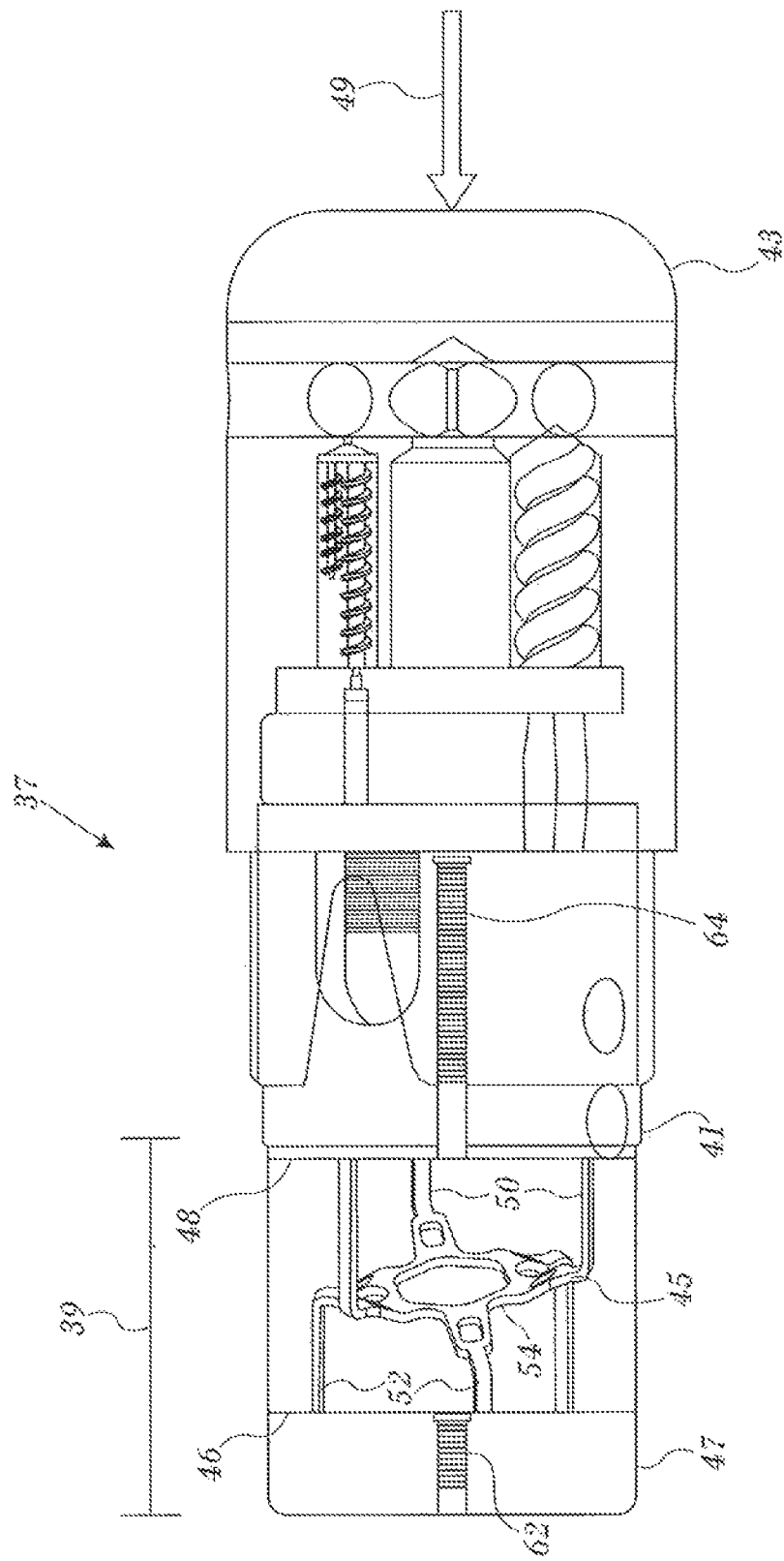
FIG. 2 is a schematic view of a distal portion of a cardiac catheter having a contact force sensor in accordance with an embodiment of the invention.

Reference is now made to FIG. 2, which is a schematic view of the distal portion of a cardiac catheter 37 in accordance with an embodiment of the invention. A contact force sensor constructed in accordance with an embodiment of the invention is disposed in a portion 39 of the catheter. Except for the contact force sensor, the catheter 37 may be the catheter described in commonly assigned U.S. Patent Application Publication No. 2009/0093806 by Govari et al., which is herein incorporated by reference. The catheter 37 is a flexible insertion tube, having a distal portion 41 for insertion into a body cavity of a patient, and a distal tip 43, which is configured to be brought into contact with tissue in a body cavity. A resilient member 45 couples a proximal portion 47 to the distal portion 41. In this disclosure members such as the proximal portion 47 and the distal portion 41, which move with in relation to one another and attach to the resilient member 45 are sometimes referred to as "connecting elements". The terms "proximal" and "distal" are used arbitrarily herein to distinguish portions of the catheter. These terms have no physical meanings with respect to the actual configuration of the catheter itself.

The distal portion 41 can move and deflect relative to the proximal portion 47 in response to pressure exerted on the distal tip 43, indicated by arrow 49. In the embodiment of FIG. 2 the resilient member 45 is interposed between two connecting elements 46, 48. Legs 50, 52 extend in opposite perpendicular directions from a plane of ring portion 54 and contact the end surfaces of the connecting elements 46, 48 so that the electromagnetic coils are spaced apart by a distance that can be as small as 0.1 mm. Electromagnetic coils 62, 64 are provided on each side of the resilient member 45 to measure displacement of the distal tip 43 relative to the proximal portion 47 of the catheter 37, as the resilient member 45 deforms in response to tip pressure.

First Embodiment

Figure 3:
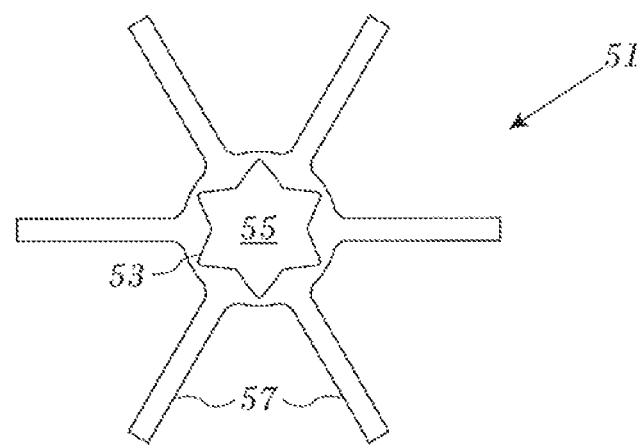
FIG. 3 is an elevation of a spring form prior to shape-setting in accordance with an embodiment of the invention.

Reference is now made to FIG. 3, which is an elevation of a spring form 51 prior to shape-setting in accordance with an embodiment of the invention. The form is cut from sheet metal, such as thin-film sputtered or cold worked nitinol and then formed or shape-set to the desired shape. Alternatively, the form can be made from a beryllium-copper alloy, cobalt chromium alloy, or stainless steel alloy. One way of accomplishing shape-setting is subjecting the form to elevated temperatures in an oven. The temperatures and other operating conditions required for shape-setting are well known in the art, according to the material used for the spring, for example nitinol is typically raised to an elevated temperature of 520 C for 30 minutes time and then quenched. Alternatively, the sheet metal can be subjected to progressive stamping, i.e., performing a series of operations on the metal with a different dies until a completed spring form has been achieved. The form 51 has a central ring portion 53 that forms a closed curve bounding an interior open space 55 having a scalloped contour. Six legs 57 radiate outward from the open space 55. Stamping may include hot forming the metal.

Referring again to FIG. 2, the ring portion 54 constitutes an elastic portion that acts as a compression spring between the proximal portion 47 and the distal portion 41 of the catheter 37. The action of the spring correlates compressive force with a displacement of the distal portion 41 relative to the proximal portion 47. The legs 50, 52 form an attachment portion to connecting elements 46, 48. In the embodiment of FIG. 2, the legs 50, 52 provide a desired separation between the distal portion 41 and the proximal portion 47. In one type of catheter, an electrode is found in the distal portion and the catheter shaft forms the proximal portion.

Figure 4:
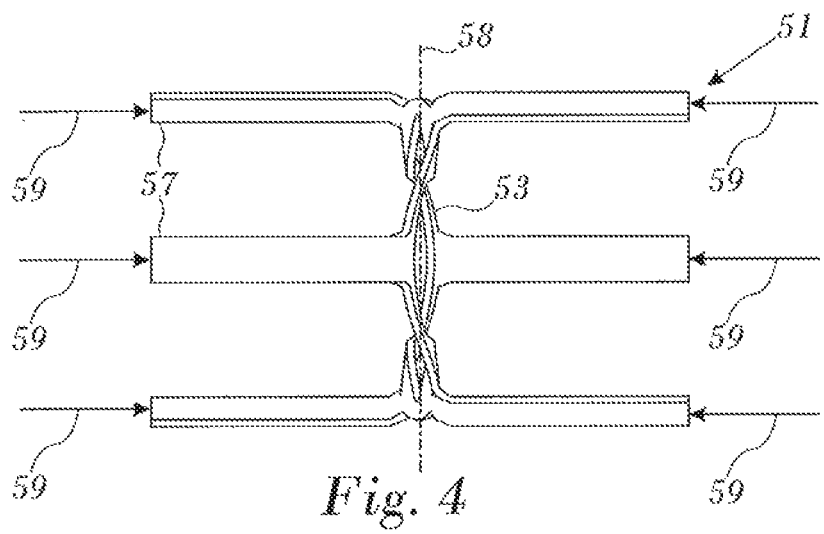
FIG. 4 is a side elevation of the form shown in FIG. 3 after shape-setting in accordance with an embodiment of the invention.
Figure 5:
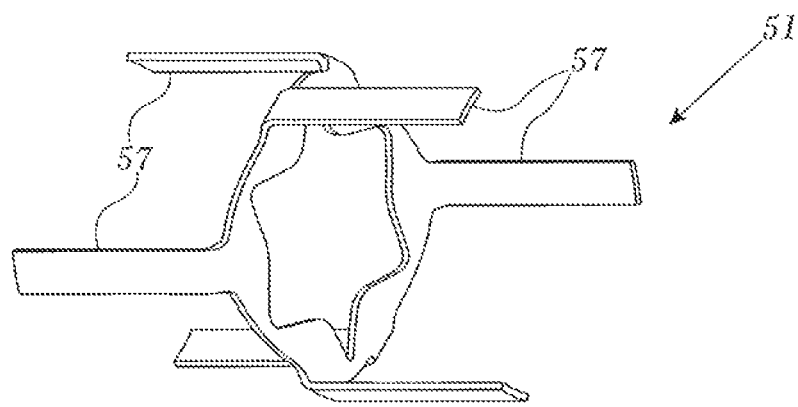
FIG. 5 is an oblique view side elevation of the form shown in FIG. 4 in accordance with an embodiment of the invention.

Reference is now made to FIG. 4 and to FIG. 5, which are a side elevation and an oblique view of the form 51, respectively. The form 51 has been shape-set in a resting position in accordance with an embodiment of the invention. Legs 57 are bent at 90° angles to plane 58 (indicated by a broken line) of the ring portion 53 in alternate directions. Moreover segments of the ring portion 53 are disposed on one side of the plane 58. When a compressive force is applied to the legs 57, as indicated by arrows 59, the ring portion 53 undergoes a deformation wherein the ring portion 53 tends to approximate a flattened state and all portions approach or lie on the plane 58. When the compressive force is removed the ring portion 53 returns to the configuration of FIG. 4.

This embodiment and the following embodiments can be mass produced to reduce unit cost. The designs are cut, stamped, or otherwise formed from planar sheet metal and shape-set into their final forms. The typical thickness dimensions for such springs in a cardiac catheter application are around 0.5 mm. Minimizing thickness of the elastic portion of the spring is important in cardiac catheters, as the two connecting elements typically contain a transmitter and a receiver, which can now be separated by a distance that does not exceed 1.5 mm. Moreover, by laser-cutting the sheet metal into a pattern, no welds are necessary, which keeps unit cost low, as well as improving reliability relative to conventional welded springs.

Second Embodiment

Figure 6:
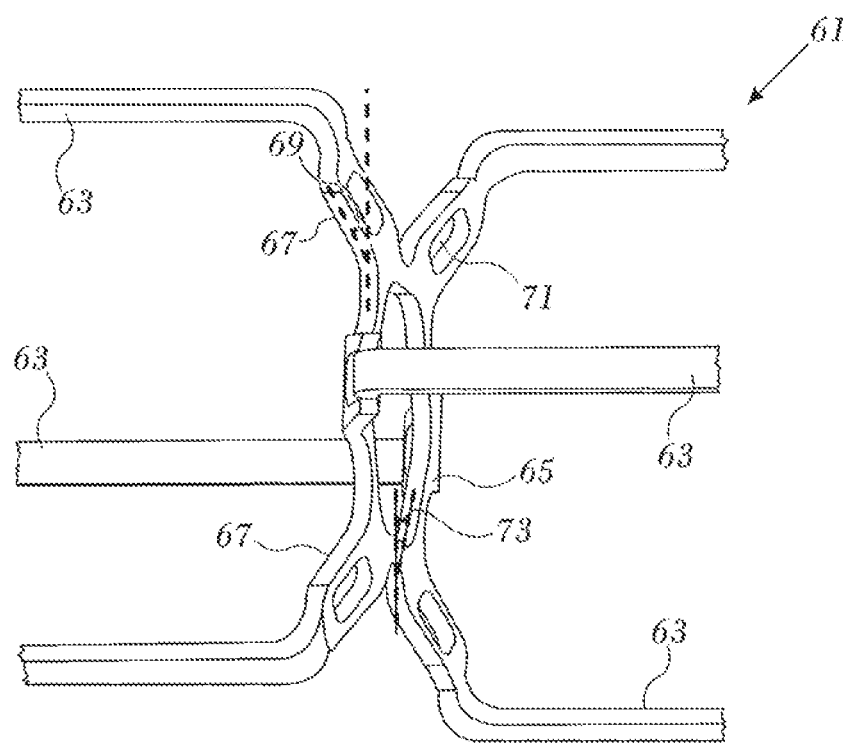
FIG. 6 is an oblique elevation of a shape-set spring in accordance with an alternate embodiment of the invention.
Figure 7:
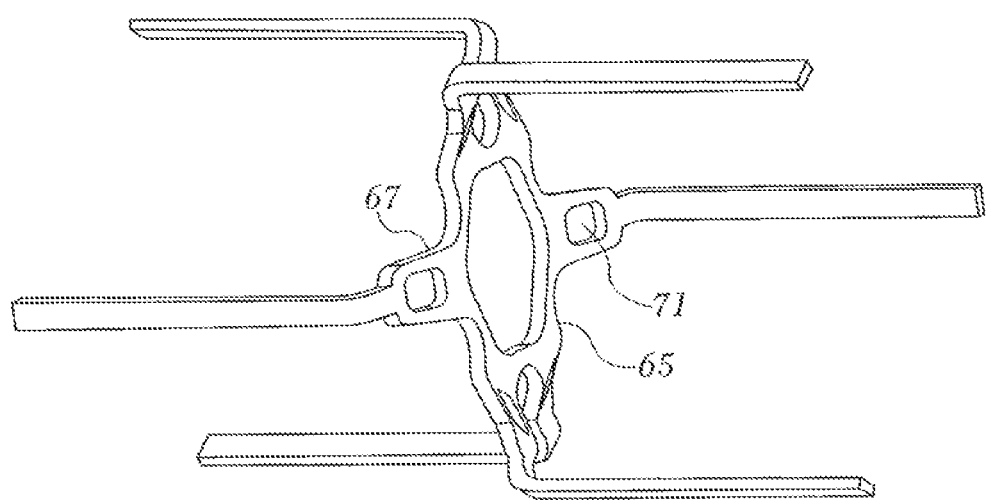
FIG. 7 is an elevation of the shape-set spring shown in FIG. 6 with greater obliquity in accordance with an alternate embodiment of the invention.

Reference is now made to FIG. 6 and FIG. 7, which are elevations of a shape-set spring 61, in accordance with an alternate embodiment of the invention. In this embodiment legs 63 are connected to central ring 65 by links 67 that form angles 69, 73 on opposite sides of the plane of the central ring 65, typically 26 degrees from the plane. The links 67 include fenestrations 71, which provide increased axial displacement with minimal effect on radial (or lateral) displacement. Compressive forces applied to the legs 63 cause reduction in the angles 69, 73, which is reversed when the compressive forces are removed.

Third Embodiment

Figure 8:
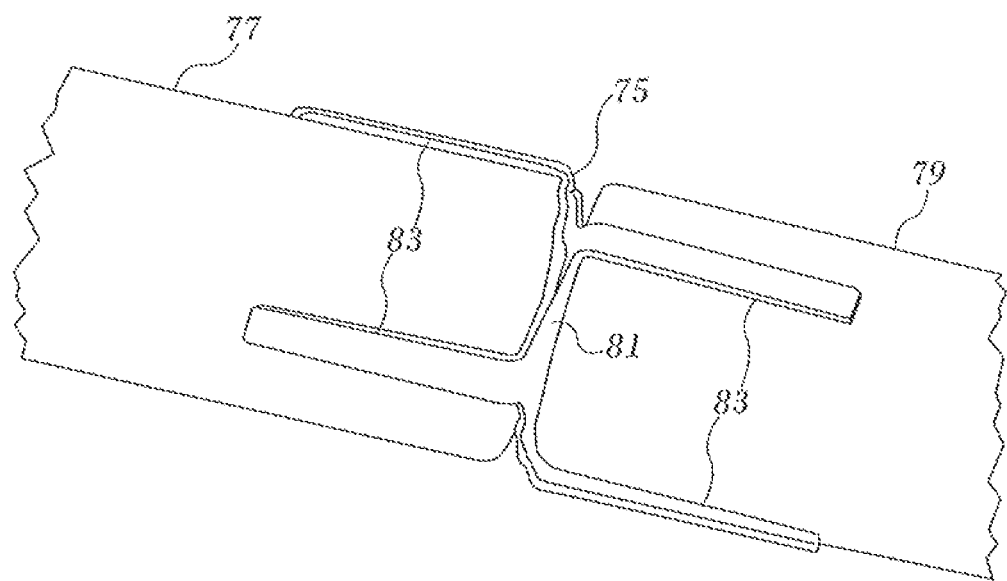
FIG. 8 is an elevation of a compression spring positioned between two cylinders in accordance with an alternate embodiment of the invention.

Reference is now made to FIG. 8, which is an elevation of a compression spring 75 positioned between two cylinders 77, 79 in accordance with an alternate embodiment of the invention. The spring 75 can be any of the embodiments hereof. Its central portion 81 functions as a compression spring as described above. The cylinders 77, 79 are embraced by legs 83, which have a holding or grasping function, securing the spring 75 to the cylinders 77, 79.

Fourth Embodiment

Figure 9:
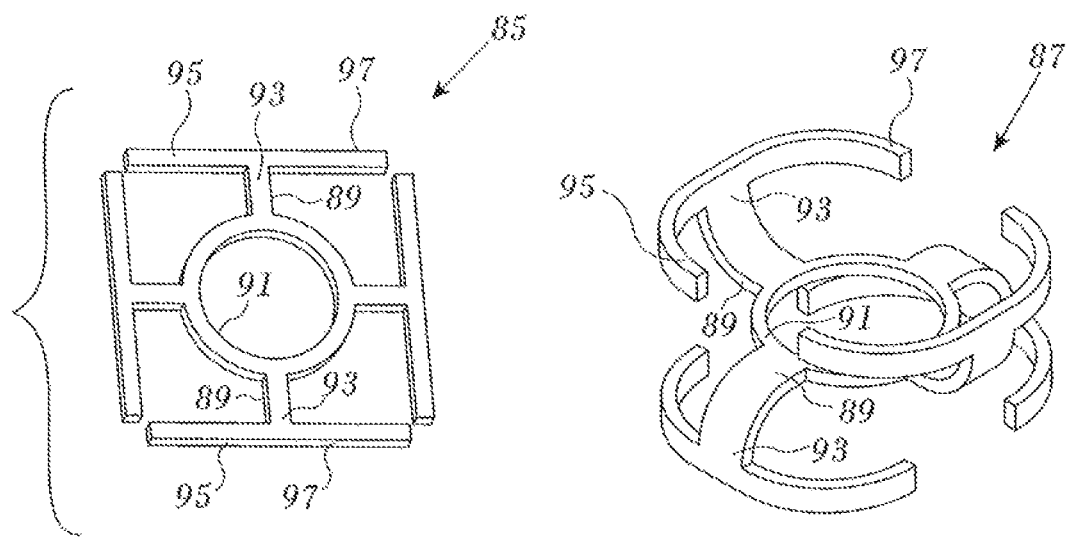
FIG. 9 illustrates a spring form and a shape-set spring in accordance with an alternate embodiment of the invention.

Reference is now made to FIG. 9, which is illustrates a spring form 85, and a shape-set spring 87 prepared from the spring form 85 in accordance with an alternate embodiment of the invention. In this embodiment legs 89 extend from a central ring 91 and bifurcate at junctions 93 to form branches 95, 97.

In the spring 87, four legs 89 have been bent above and below the plane of the ring 91 as described in the previous embodiments. In some applications the legs 89 keep respective contacting structures, e.g., distal portion 41 and proximal portion 47 of a catheter (FIG. 1) spaced apart. The branches 95, 97 are bent inward for other applications in order to provide a holding or grasping function similar to the spring 75 (FIG. 8).

Fifth Embodiment

Figures 10, 11:
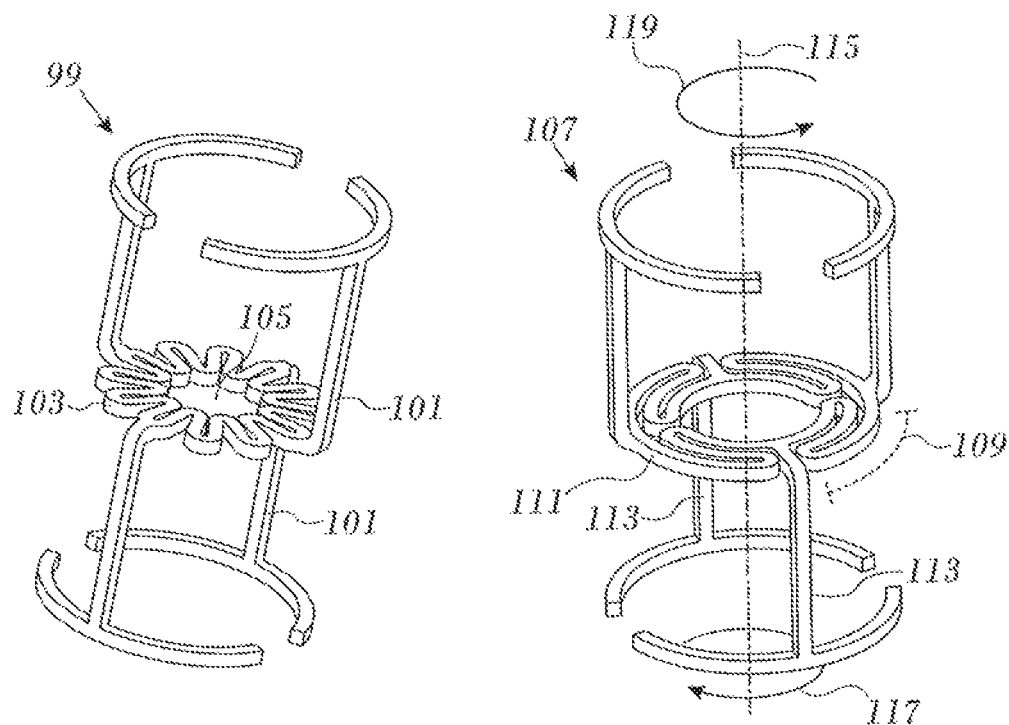
FIG. 10 illustrates a shape-set spring in accordance with an alternate embodiment of the invention.
FIG. 11 illustrates a shape-set spring in accordance with an alternate embodiment of the invention.

Reference is now made to FIG. 10, which illustrates a shape-set spring 99, in accordance with an alternate embodiment of the invention. The structure of the spring 99 is similar to the spring 87 (FIG. 9), with four legs 101 except that central ring 103 is deformed into a sinusoidal configuration in which oscillations occur in a generally radial direction, toward and away from a center point 105 of the central ring 103. The length dimension exceeds the circumference of circular ring of like diameter, and it allows for even tighter placement between the transmitter and receiver coils.

Sixth Embodiment

Reference is now made to FIG. 11, which illustrates a shape-set spring 107, in accordance with an alternate embodiment of the invention. This variant is similar to the embodiment of FIG. 10, except that sectors 109 (one of the sectors 109 is indicated by a broken curve) of a central ring 111 that connect legs 113 are elaborated into two hairpin curves. The spring 107 is capable of acting as a compression spring as described above, and can also function to allow lateral (or radial) movement.

Seventh Embodiment

Figure 12:
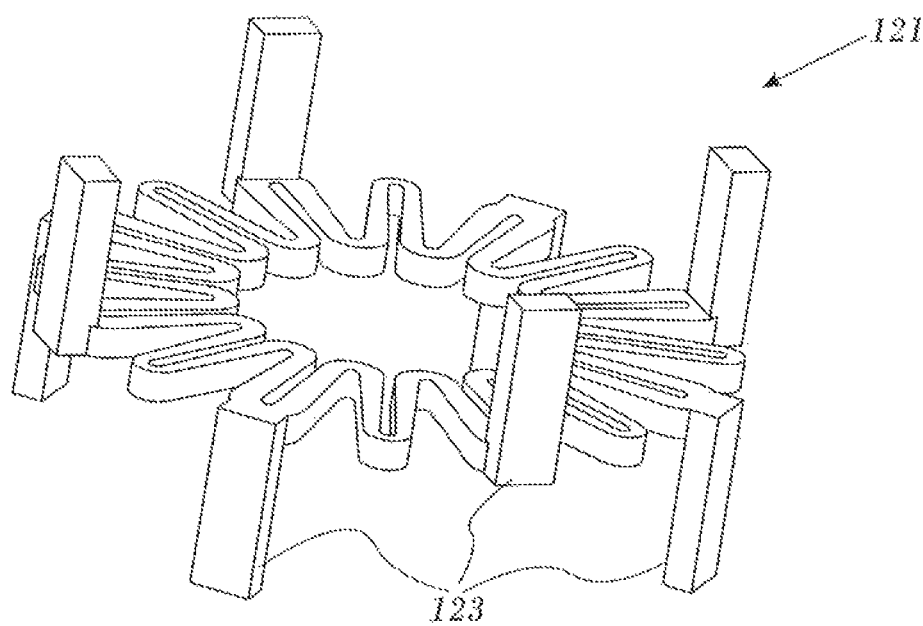
FIG. 12 illustrates a shape-set spring in accordance with an alternate embodiment of the invention.

Reference is now made to FIG. 12, which illustrates a shape-set spring 121, in accordance with an alternate embodiment of the invention. The arrangement is similar to the spring 99 (FIG. 10), except there are six legs 123 instead of four. This design enables the spring 121 to withstand relatively large compressive forces compared with the spring 99.

Eighth Embodiment

Figure 13:
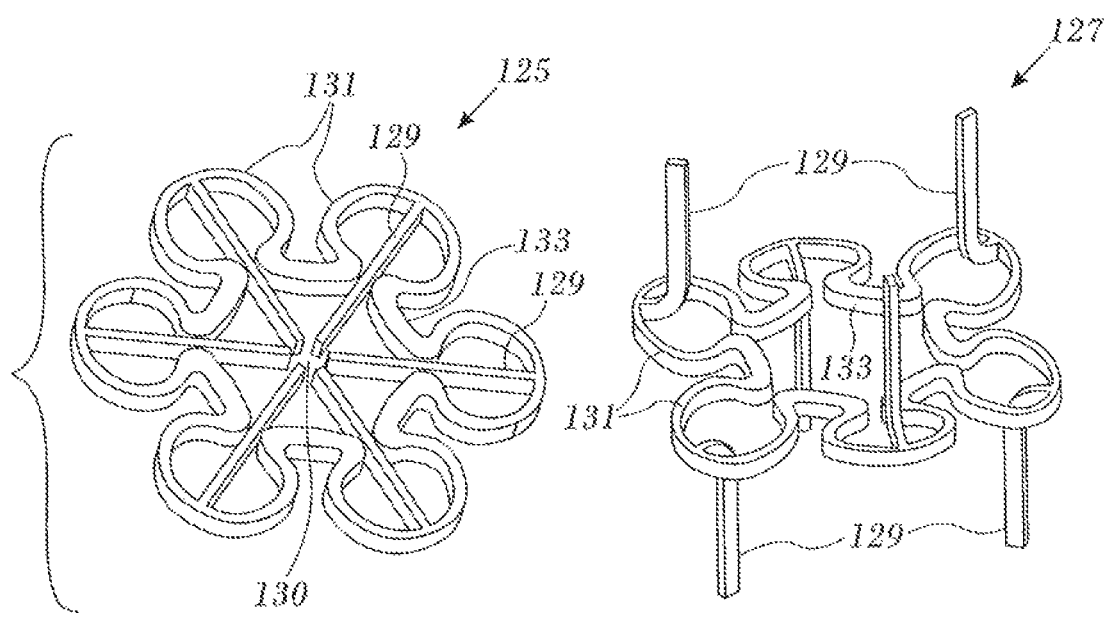
FIG. 13 illustrates a spring form and a shape-set spring in accordance with an alternate embodiment of the invention.

Reference is now made to FIG. 13, which is illustrates a spring form 125 and a shape-set spring 127 prepared from the spring form 85 in accordance with an alternate embodiment of the invention. In this embodiment six legs 129 attach to outwardly directed loops 131 formed in a central ring 133. As shown on the left side of FIG. 13, the six legs 129 extend inward toward the center 130 of the central ring, which reduces the outer diameter of the final formed spring form 125.

Ninth Embodiment

Figure 14:
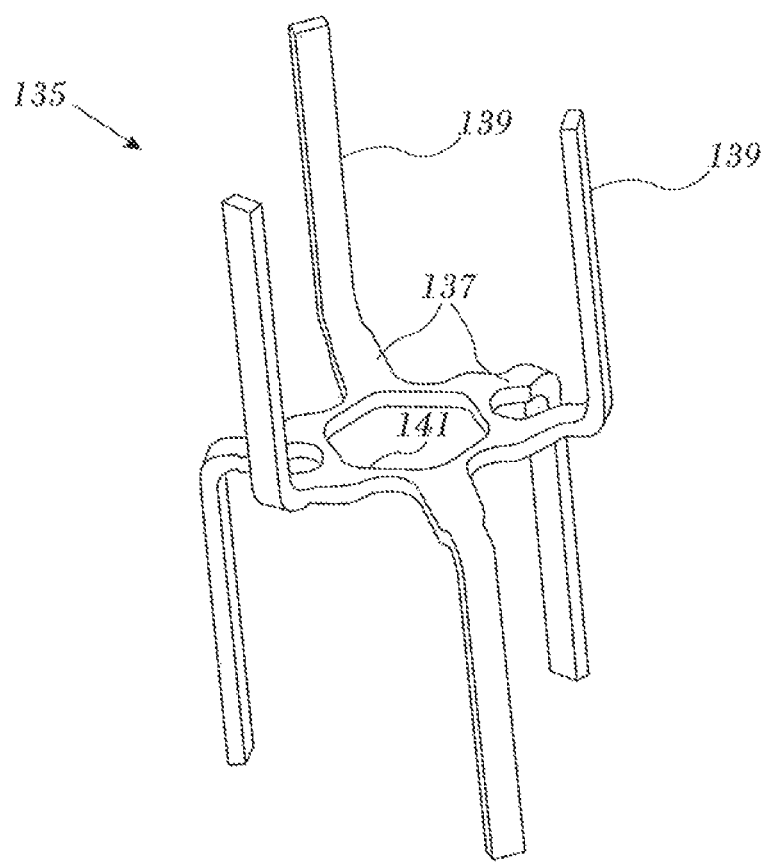
FIG. 14 illustrates a shape-set spring in accordance with an alternate embodiment of the invention.

Reference is now made to FIG. 14, which illustrates a shape-set spring 135 in accordance with an alternate embodiment of the invention. This embodiment is similar to the spring 61 (FIG. 6), except that links 137 connecting legs 139 with center ring 141 are solid rather than fenestrated, which makes the process simpler for a metal stamping operation.

Tenth Embodiment

Figure 15:
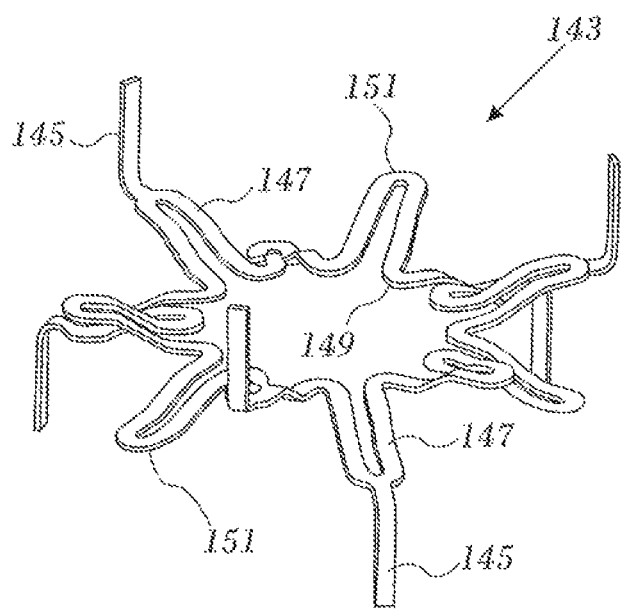
FIG. 15 illustrates a shape-set spring in accordance with an alternate embodiment of the invention.

Reference is now made to FIG. 15, which illustrates a shape-set spring 143 in accordance with an alternate embodiment of the invention. In this embodiment there are six legs 145, attached to respective elongated loops 147 that extend from a central ring 149. Besides the loops 147, the ring 149 comprises additional outwardly extending loops 151 that alternate with the loops 147 and do not attach to legs. The additional loops decrease stiffness and spread the stresses over a larger area, resulting in a more robust design.

It will be appreciated by persons skilled in the art that the present invention is not limited to what has been particularly shown and described hereinabove. Rather, the scope of the present invention includes both combinations and sub-combinations of the various features described hereinabove, as well as variations and modifications thereof that are not in the prior art, which would occur to persons skilled in the art upon reading the foregoing description.

The invention claimed is:

1. A catheter having a contact force sensor, comprising:
a flexible insertion tube, having a proximal portion and a distal portion for insertion into a body cavity of a patient; and
a resilient member, which couples the proximal portion of the insertion tube to the distal portion, wherein the resilient member comprises a central ring structure and independent legs that project and extend in opposite perpendicular directions from a plane defined by the central ring structure and in alignment with the insertion tube, the resilient member being formed from a shape-set elastic material, the legs being configured to be in contact with the proximal portion and the distal portion of the insertion tube, respectively, wherein a compressive force to the resilient member applied through the distal portion of the insertion tube to the independent legs produces a deformation of the resilient member that correlates with a displacement of the proximal portion relative to the distal portion, wherein the resilient member is connected through its legs to coils that measures the displacement.

* * * * *